United States Patent [19]

Wilde et al.

[11] Patent Number: 4,917,966
[45] Date of Patent: Apr. 17, 1990

[54] GALVANIC PROTECTION OF STEEL WITH ZINC ALLOYS

[75] Inventors: Bryan E. Wilde, Granville, Ohio; Michael K. Budinski, Rochester, N.Y.

[73] Assignee: The Ohio State University, Columbus, Ohio

[21] Appl. No.: 256,187

[22] Filed: Oct. 7, 1988

Related U.S. Application Data

[63] Continuation of Ser. No. 017,810, Feb. 24, 1987, abandoned.

[51] Int. Cl.⁴ .............................................. B32B 15/00
[52] U.S. Cl. .................................... 428/659; 420/520; 420/513; 420/434; 427/433
[58] Field of Search ................ 420/434, 520; 428/659; 427/433

[56] References Cited

U.S. PATENT DOCUMENTS 4,252,866  2/1941  Matsudo ............................. 428/659
4,650,724  3/1987  Umino ................................ 428/659

FOREIGN PATENT DOCUMENTS 28900    9/1975  Japan .................... 427/433
0007333  1/1977  Japan .
0082691  5/1985  Japan .................... 428/659
0138093  7/1985  Japan .................... 428/659

Primary Examiner—Sam Silverberg
Attorney, Agent, or Firm—Frank H. Foster

[57] ABSTRACT

Galvanic protection of steel is provided by means of coupling thereto of zinc binary alloys of Zn/8 to 18% wt. Co or Zn/20 to 50% wt. Mn with teachings of method of protection, the protected steel having the alloy coupled thereto, as well as the alloys per se. Also, a technique for determining alloys useful for the cathodic protection is taught with the technique including determining the critical cathodic protection potential for steel and the galvanic current and corrosion potential for candidate binary Zn alloy compositions followed by coupling to the steel of one such alloy composition whose determined corrosion potential is lower than the critical corrosion potential for the steel in the corrosive environment in which protection is sought.

7 Claims, 8 Drawing Sheets

GALVANIC PROTECTION OF STEEL WITH ZINC ALLOYS

This is a continuation, of application Ser. No. 017,810, filed Feb. 24, 1987 now abandoned.

This invention relates to protection of steel from corrosion by certain essentially binary zinc alloys, and includes not only the alloys for providing the protection, but also a procedure with determination of criteria for establishing which binary zinc alloys are suitable and useful, as well as using the alloys for galvanic protective purposes and also an assembly of steel galvanically coupled to the alloy. More particularly, the invention concerns certain zinc-cobalt and zinc-manganese essentially binary alloys providing improved galvanic corrosion resistance for steel compared to zinc per se, their use to cathodically protect steel, and these alloys galvanically coupled to steel.

BACKGROUND

Zinc coatings have been in use for many years as an effective means of controlling the corrosion of steel. Due to the protective effect of galvanic coatings, the use of galvanized steel has increased markedly.

In recent years automobile manufacturers, designing lighter weight, corrosion resistant vehicles, have stimulated the use of galvanized steel. A drive to reduce the weight of vehicles calls for the use of high-strength, low-alloy steels with thinner wall thicknesses. The use of thinner sheet steel requires additional corrosion resistance providable through the use of galvanic coatings. Automobile manufacturers are also interested in the forming of coated sheet steel for autobody panels. Forming coated steel requires a relatively thin galvanic coating. Because of the relatively high galvanic and self corrosion of coatings of zinc per se, thick coatings have been necessary. To improve the formability of such protectively coated steel, the thick zinc coating desirably should be replaced with a thin, more corrosion resistant coating with improved galvanic protective properties.

The use of galvanic coatings is increasing in other areas also, such as reinforcing bars for concrete structures. It has been documented that corrosion of steel rebar due to halide salts within the concrete is the basis for the formation of potholes and cracked concrete. Coating the steel with a high performance galvanic coating is one proposal to alleviate this problem.

It is obvious that the increasing use of galvanized steel puts great emphasis on the performance of galvanic coatings. Although pure zinc coatings adequately protect steel, they have several drawbacks including:

(1) The widely differing electrode potentials between zinc and steel [−1.05 Vsce (Volts versus a saturated calomel reference electrode) and −0.69 Vsce respectively in aerated salt water solutions] result in excessive galvanic corrosion, where the zinc actually overprotects the steel.

(2) Hydrogen gas evolution may occur due to the large cathodic overvoltage. In some instances this may impair the mechanical properties of steel. An example of this is a steel reinforcement bar in concrete.

(3) Painted galvanized steel experiences rapid paint undercutting and delamination due to the excessively large cathodic overvoltage and corrosion product wedging.

(4) The self corrosion rate of zinc is relatively high in certain environments.

The aforementioned problems with zinc coatings are from a corrosion standpoint. Other concerns with coatings in general are: weldability, spangle (grain size), formability, paintability, and brittle intermetallic layers.

From the foregoing, it is apparent that opportunity exists for considerable improvement over the use of pure zinc coatings for corrosion protection of steel. Relatively recently some improvement has been reported in this area by using an electroplated zinc-manganese alloy (M. Sagiyama, T. Urakama, T. Adaniya and T. Hara, "Zinc-Manganese Alloy Electroplated Steel for Automotive Body", paper 86028, SAE International Congress and Exposition", Detroit, Mich., Feb. 24–28, 1986).

The present invention will teach a unique electrochemical technique for the development of galvanic coating alloys. Through its use, several new galvanic coating zinc alloys with improved corrosion resistance have been provided, as will be apparent from what follows.

SUMMARY STATEMENT OF THE INVENTION

Steel, e.g. DQSK steel, was protected from galvanic corrosion in an aqueous salt environment by coupling the steel with an alloy selected from the group of alloys consisting essentially of (i) 8 to 18 percent by weight of cobalt balance of zinc, and (ii) 20 to 50 percent by weight of manganese and a balance of zinc. Desirably, the coupling is with the alloy as a coating adhering to the steel, and preferably the Zn/Co alloy contain about 11 to 16 percent by weight of cobalt and the Zn/Mn alloy contains about 25 to 40 percent by weight manganese.

The invention includes the manufacture, or assembly, of steel coupled, desirably coated, with the alloy. The invention also teaches the alloy composition.

The invention additionally provides a method for determination of a metal alloy composition for galvanic protection of steel (other than stainless steels), and the providing of a galvanically protected steel by (a) placing a specimen of the steel, generally immersed, in the environment in which protection is to be provided and while within that environment determining its critical cathodic protection potential, (b) preparing or otherwise fabricating in bulk form a plurality of alloy specimens including those of varied compositions in which alloy components have been increased in incremental amounts, (c) placing these specimens individually in the same environment used to determine the critical cathodic protection potential of the steel and, while therein, measuring for each its galvanic current and corrosion potential at a time when corrosion of each has reached a substantially steady state rate, and (d) subsequently coupling to the steel of an alloy of a composition which in step (c) provided a determined corrosion potential lower than the critical cathodic protection potential for the steel as determined in step (a).

BRIEF DESCRIPTION OF THE DRAWINGS

In the included drawings, a number of the figures present in schematic-like fashion various apparatuses, cell configurations and circuitry; other set-ups and the like, with it believed readily apparent from applicants' presented figures and disclosure to one of ordinary skill in the art how to assemble and provide the specific item illustrated in the particular figure. Accordingly.

DETAILED DESCRIPTION OF THE INVENTION

Figure 2:
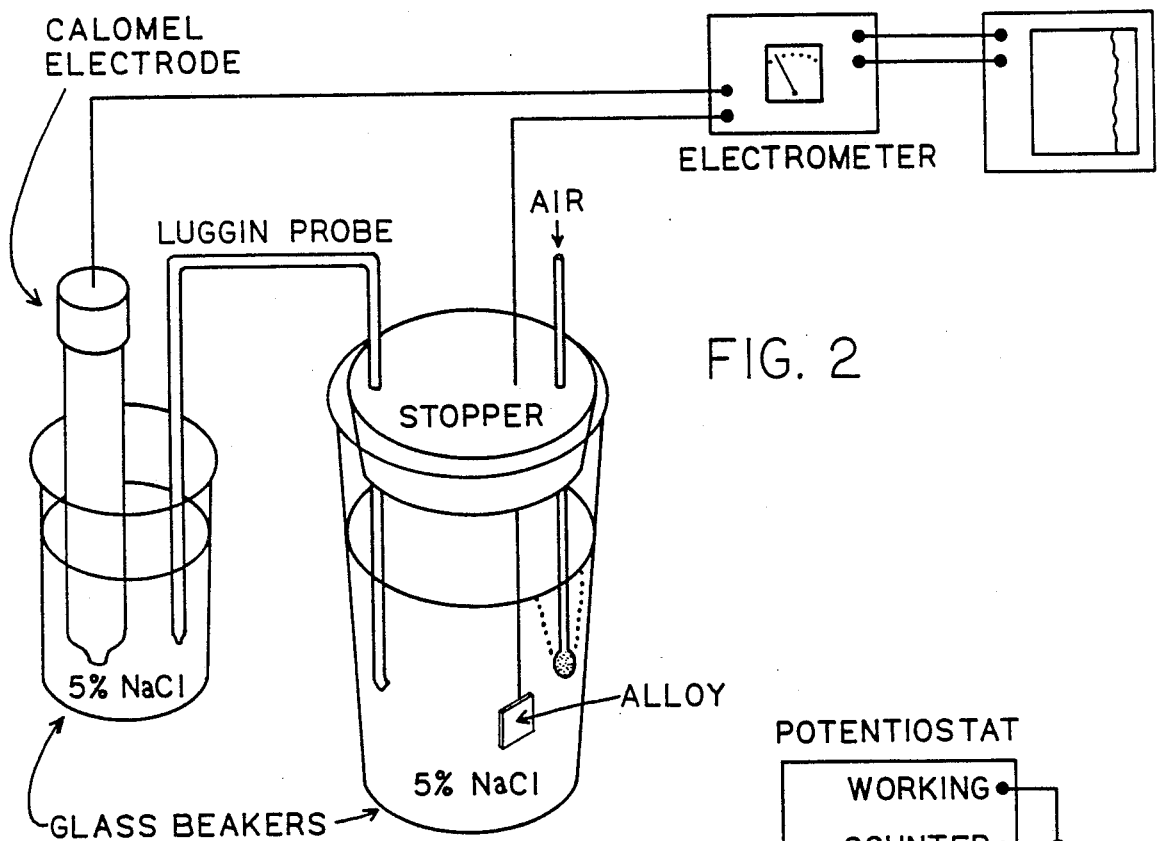
FIG. 2 presents a corrosion cell configuration for open circuit anode potential measurements.

The present invention utilizes an approach and technique as follows: Bulk alloys, rather than actual coatings, were used to determine useful and optimal composition. The invention determined the critical cathodic protection potential, which is a new criterion for the development of galvanic coatings. This is believed to not have been reported previously in the literature. This criterion was determined under conditions that mimic the environment (e.g. salt spray). It is important to note that the critical cathodic protection potential is valid only under conditions at which it was determined, e.g. continuous immersion in aerated 5% NaCl solution at 30 C.

The solution potential, galvanic corrosion current and coupled potential versus composition maps are also determined and apparently are new to the galvanic coating technology practices. This new information dictates what alloy compositions will cathodically protect steel and the optimal alloy composition. For the screening of potential galvanic coating alloys the approach and techniques reported herein are quite useful. In comparison to such tests as the ASTM B 117 salt spray test, this approach is less time consuming and gives quantitative data.

The polarization work here is rather unique since very little polarization work has been reported in the literature on galvanic coating alloys. In general, the current densities associated with the polarization of zinc and zinc alloys are several orders of magnitude higher than those of aluminum. The polarization studies also give insight as to how the alloying elements added to zinc reduce or increase the galvanic current. In general, alloying elements added to zinc increased zinc's polarizability and shifted open circuit potentials to more noble values, thereby reducing the galvanic current.

Through the invention, it was possible to make evaluations as to certain binary zinc alloys which are useful and will perform well as galvanic coatings on steel. The following TABLE I lists two particularly promising alloys for such a purpose.

TABLE I

| PROMISING GALVANIC COATING ALLOYS | | | |
|---|---|---|---|
| ALLOY COMPOSITION | CORROSION Rate μA/sq cm | GALVANIC CURRENT μA | COUPLED POTENTIAL Vsce |
| Zn-8 to 18 Co | 370 | 30 | −.77 |
| Zn-30 Mn | 430 | 50 | −.85 |

In general, the determined useful zinc binary alloy is selected from the group of alloys consisting of 8 to 18 by weight of cobalt and a balance of zinc, and 20 to 50 percent by weight of manganese and a balance of zinc. Particularly preferred are the alloy compositions set forth in the preceding TABLE I. Also preferred, as apparently being optimum, are Zn/about 11 to 16% wt. Co and Zn/about 25 to 40% wt. Mn.

The approach taken in the invention provides for the determination of a coating composition from a corrosion standpoint by means of continuous immersion. The procedure was:

1. Determination of the critical cathodic potential required for effective protection of steel (the substrate). This potential was used as a criterion for galvanic coating alloy development.

2. Fabrication of bulk zinc binary coating alloys and measurement of the corrosion potential as a function of composition for each of the alloy systems. Cobalt or manganese, or certain other binary alloy additions, modified the corrosion behavior of zinc. The resultant potential vs. composition maps are basically a galvanic series for each alloy system.

3. Perform zero resistance ammeter tests to determine the galvanic current and coupled potential for each of the alloys. A 3.7:1 area fraction steel to coating alloy relation was used. Graphs of coupled potential and galvanic current as a function of alloy composition were plotted.

4. Using the criterion developed in step 1, the optimal coating compositions were determined from a galvanic corrosion standpoint. Polarization curves of the optimal alloys were then obtained to determine the self corrosion rate and polarization behavior of the alloy.

5. The optimal coating will protect steel to the critical cathodic overpotential, transfer minimal but adequate galvanic current and have a low self corrosion rate.

It is believed to be well accepted in the cathodic protection art that simulated evaluations using electrochemical method are highly useful to determine and simulate actually useful galvanic coatings. It is asserted that as taught herein, those determinations and simulations provided to teach the invention, do mimic and do provide teachings highly indicative of the utility of the invention in the cathodic protection art.

Although the illustrative simulations include data collected when the steel and zinc binary alloys are coupled electrically by means of a wire and an electrolytic solution (e.g. 5% aqueous NaCl), such a coupling could just as well for end utility be an actual adherent coating of the binary alloy on the substrate (i.e. steel). It should be recognized that the corrosion performance of steel and galvanic alloys is very similar in solution of NaCl in the concentration range 35 to 5 percent by weight. Such binary zinc alloys are contemplated as applicable to steel as coatings by at least one or more of the following techniques of electroplating, flame spraying, hot dipping, sheradizing, and the like.

DETERMINATION OF THE CRITICAL CATHODIC PROTECTION POTENTIAL

Figure 1:
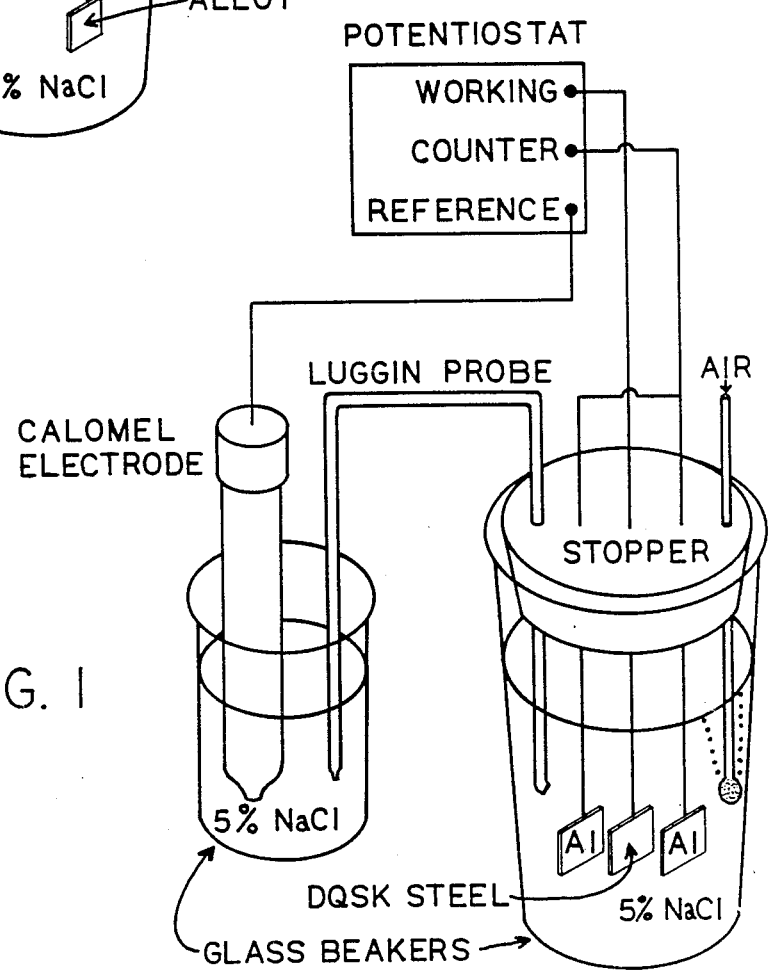
FIG. 1 illustrates an apparatus set-up for the determination of the critical cathodic potential of DQSK steel.

Paddle specimens of steel with known surface area were exposed to a 5 weight percent sodium chloride solution, at 25 C, using the system illustrated in FIG. 1. The entire unit was enclosed in air thermostat, which controlled the temperature to +/−1 C. A given volume of solution was introduced and saturated with air at a constant flow rate of 100 ml/min. The potential of the steel was controlled at the chosen value with a Wenking TS 3 potentiostat. Auxiliary electrodes of 1100 grade aluminum were located on either side of the steel. All potentials were measured with reference to a saturated calomel electrode, with no correction for junction potentials.

Specimens were exposed for various periods, then removed from the solution. Because the corrosion products were in the form of rust ($Fe_2O_3$ all of the products from the test beaker were dissolved in warm, inhibited 25 volume percent HCl (inhibited with Rhodamine B). In separate tests, this procedure failed to produce any corrosion products from the steel during descaling. The total iron corrosion product dissolved, in 25 volume percent HCl, was made up to 1000 ml volume in a standard flask. The iron content of the solution was measured using a Perkin-Elmer Atomic Absorption Spectrophotometer with a specific iron electron gun.

Corrosion rates were calculated using the following relationship $$mpy = \frac{534}{DAT}$$

where W is the total weight of iron corrosion product found (mg) after exposure time T (hr), D is the density of carbon steel (7.86 g/cc) and A ($in^2$) is the area of the original paddle specimen.

All solutions were made using doubly deionized water and reagent grade chemicals.

CORROSION POTENTIAL MEASUREMENTS

The corrosion potential for each of the specimens was measured in air saturated 3.5 weight percent sodium chloride solution. This solution models road salt, sea water and salt spray conditions. The solution was air saturated in order to further model these conditions. Each specimen was prepared for immersion by degreasing in acetone and sanding with 400 grit abrasive. The corrosion cell used is shown in FIG. 2. All potential measurements were made relative to a saturated calomel electrode (sce) via a Keithly 602 electrometer. A strip chart recorder, connected to the electrometer's lx analog output, was utilized to detect a steady-state solution potential. In the case of the specimens mounted in epoxy, the edges between the specimen and the epoxy were sealed with Miccromask (Pyramid Plastics Inc., Hope, Ark. 71801), an electroplating lacquer. A Teflon (Du Pont Co., Wilmington, DE) compression gasket and threaded rod were used to mount the threaded specimens.

ZERO RESISTANCE AMMETER MEASUREMENTS

Figure 3:
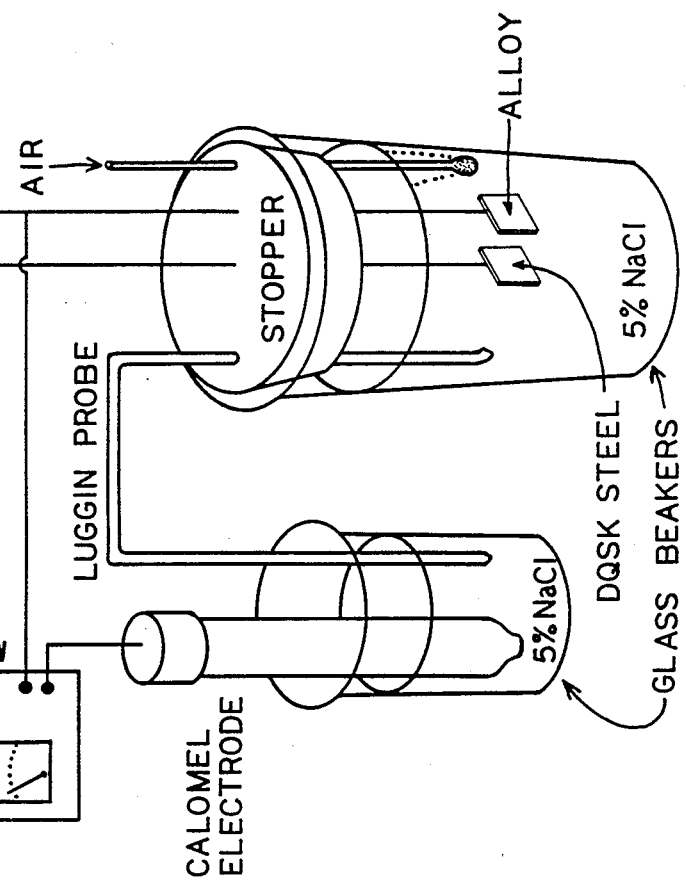
FIG. 3 shows a zero resistance ammeter set-up for determination of galvanic currents.

To measure the current transferred through a galvanic couple, a zero resistance ammeter was employed. A schematic diagram of the circuit setup along with the corrosion cell is shown in FIG. 3. A Wenking TS 3 potentiostat, a Kiethly 602 electrometer and an Esterline Angus dual pen stripchart were used to detect galvanic current and coupled potential as a function of time. Sample preparation involved degreasing the specimens in acetone and sanding them with 400 grit abrasive. In order to maintain a 3.7: 1 area fraction between the steel and the alloy, Miccromask electroplacing lacquer was used to mask the specimens.

The corrosion cell contained 250 ml of 3.5 weight percent sodium chloride solution. Air was bubbled through the solution at a rate of 35 ml/min. The exposed areas faced each other and the distance between areas was ¾ inch. The potential measurements were made relative to a saturated calomel electrode, with no correction for junction potentials.

Typically, steady state current and potential measurements were achieved between 24 and 48 hours.

POLARIZATION CURVES

Figure 4:
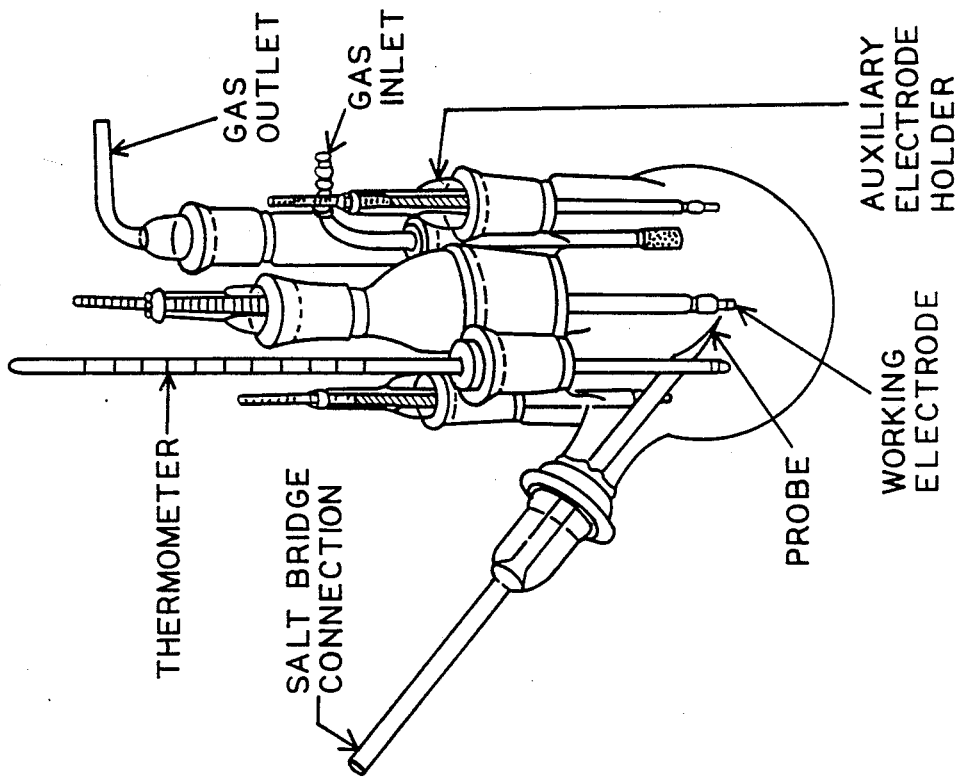
FIG. 4 illustrates a corrosion cell used for polarization studies, FIG. 5 provides a data plot of corrosion rate of DQSK steel in air saturated 5.0% sodium chloride solution at 25 C as a function of time, FIG. 6 provides a data plot of steady state corrosion rate of DQSK steel in aerated 5.0% sodium chloride solution at 25 C as a function of cathodic potential.

The metals and alloys of particular interest were subjected to potentiostatic measurements in order to obtain polarization curves. The corrosion cell used to make these measurements is shown in FIG. 4. The solution used for the tests was 3.5 weight percent sodium chloride saturated with air (45 ml/min). The test cell held 1000 ml of solution, and was maintained at a constant temperature of 25 C. During specimen immersion, the solution was purged with oil-free breathing air. The samples were prepared by degreasing in acetone and sanding with 400 grit abrasive. Specific areas were masked off using Miccromask. Exposed areas were measured to within +/−0.002 sq. cm.

Upon specimen immersion, the corrosion potential of the specimen was recorded as a function of time using a Keithly 602 electrometer and a Hewlett Packard strip chart recorder. Steady state corrosion potentials were typically achieved within 4 to 8 hours. After steady state was reached, the specimens were polarized with a Wenking TS 3 potentiostat using a 1 square centimeter platinum counter electrode facing the specimen. A scan rate of 25 millivolts in 3 minutes was maintained. Cathodic and anodic polarization curves were run as separate events.

EXAMPLE

The steel used for this example was drawing quality semikilled (DQSK) steel supplied by the U. S. Steel Co., Pittsburg, Pa. The steel was in the sheet form, 0.0255 inches thick. The average ASTM grain size of the steel was 7. This is a typical steel used for auto body panels.

Since one application of the invention is a development of improved galvanic coatings for automobiles, this choice of steel is logical and especially illustrative. The example could just as well employed another steel, e.g. carbon steel or low alloy steel, and similar illustrative results would be obtained. The only steel to which the invention is not particularly applicable are those steels customarily designated to be stainless steels and the like, with such steels and their alloys not normally provided with galvanic protection.

Special techniques were used to alloy high melting point elements with zinc, due to zinc's low melting point and high vapor pressure. The following zinc alloys were made by reacting measured amounts of the constituent elements in fused quartz tubes sealed under vacuum: Zn/Co and Zn/Mn. Several other binary zinc alloys also were prepared for comparison purposes. The elemental metals used in the alloys were reagent grade and were obtained from commercial sources. These alloys were subsequently heated to temperatures 100 C above the liquid temperature and allowed to react for five days to produce a homogeneous alloy. After five days, the liquid melt was removed from the furnace and cooled to room temperature.

The higher melting point alloys, being irregular in shape and difficult to machine, were embedded in epoxy with an electrical lead, or alternatively, when possible, were machined into cylindrical specimens $\frac{1}{2}$ inch in diameter and $\frac{1}{2}$ inch long. Internal $\frac{1}{4}$-20 NC threads were tapped $\frac{3}{8}$ of an inch into one end of the specimen.

THE CRITICAL CATHODIC PROTECTION POTENTIAL

Figure 5:
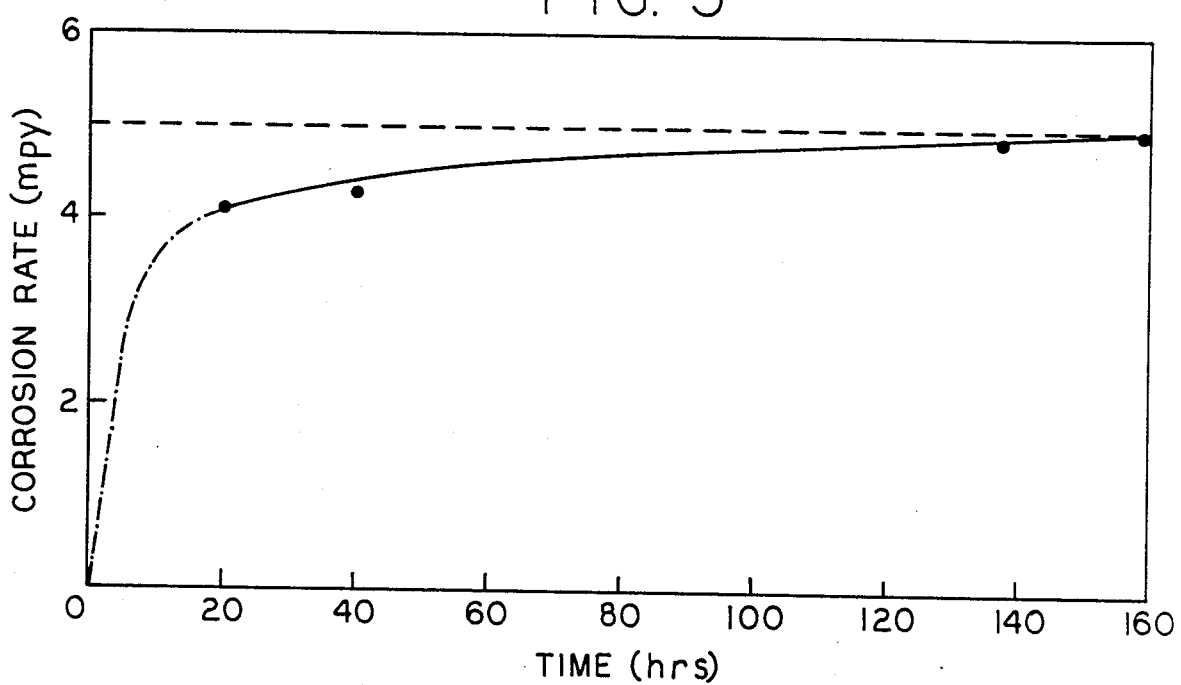

To insure that the steel was corroding at steady state, a series of tests were conducted, over a 200 hour test period with no applied potential. Samples were taken at various intervals over the 200 hours, and the results are shown in FIG. 5. It is clear that a minimum 160 hour exposure time was necessary to achieve steady state. All subsequent tests were conducted for 160 hours.

Figure 6:
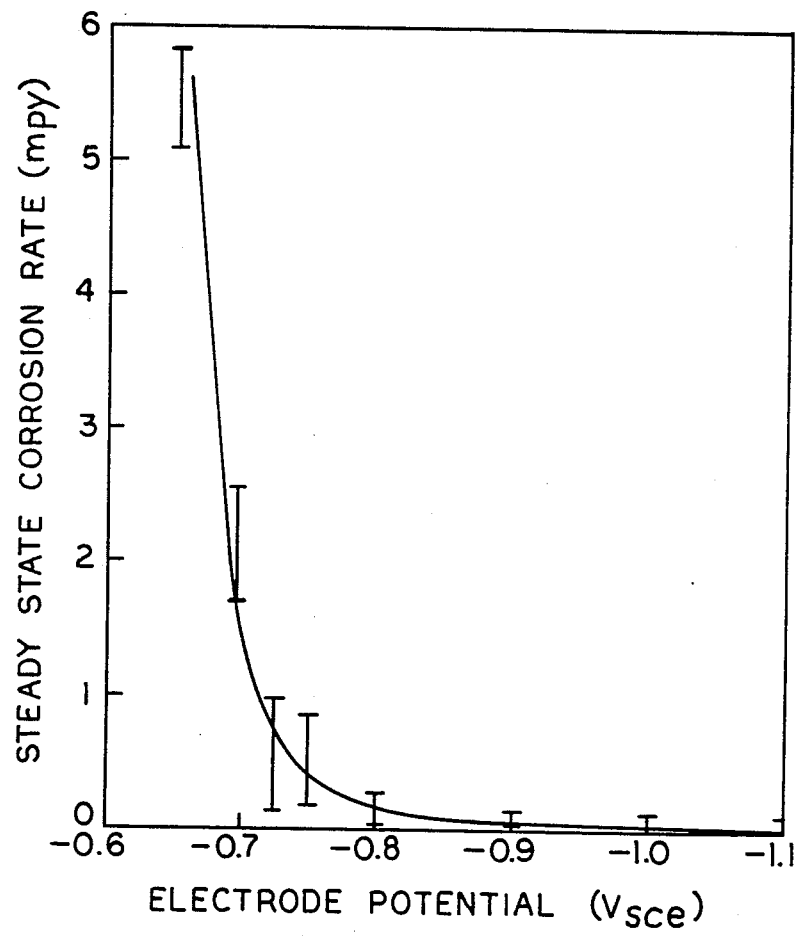

The influence of applied cathodic potential on the corrosion rate of DQSK steel is shown in FIG. 6. The error bars illustrate the variability of the data. From the figure, it is clear that a corrosion rate of less than 1 mil per year (mpy) can be achieved with an applied potential of $-0.725$ Vsce. As the applied cathodic potential was increased, the corrosion rate further decreased—essentially reading zero at $-1.1$ Vsce. It has been noted that effective cathodic protection (e.g. less than 1 mpy) may be achieved at potentials less negative than commonly accepted values. For example: the critical cathodic potential for steel in beer was found to be about $-0.700$ Vsce, and the critical cathodic potential for steel in simulated concrete environments was also found to be less negative than the commonly accepted $-0.850$ V (vs. copper/copper sulfate criterion.

The curve in FIG. 6 thus establishes that DQSK steel will receive adequate cathodic protection in aerated 5.0 wt/o sodium chloride solutions at potentials in the range of $-0.725$ to $-0.750$ Vsce. This curve also reveals the reversible potential for the cathodic partial process. This potential is in the range of 0.850 to $-0.950$ Vsce where the corrosion rate is zero.

SOLUTION POTENTIALS OF ALLOYS

The corrosion potential was determined for each of the Zn/Co and Zn/Mn alloys. Corrosion potential maps were made as a function of alloy composition. These corrosion potential maps are actually galvanic series for each of the alloy systems. Although they give no information about the degree of galvanic corrosion, they indicate the composition range in which cathodic protection may be achieved if the steel were galvanically coupled to a particular alloy.

Figure 7:
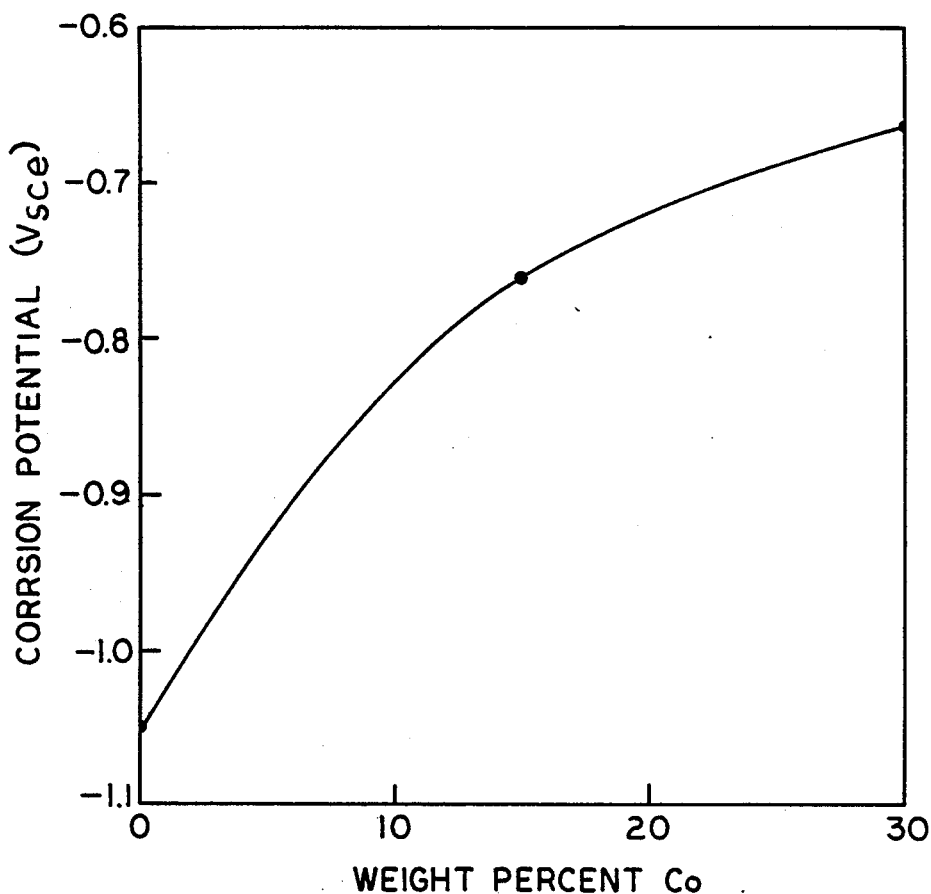
FIG. 7 presents a data plot of solution potential of zinc as a function of cobalt content in air saturated 3.5% sodium chloride solution at 25 C.

FIG. 7 displays a solution potential map for the Zn/Co alloy. Cobalt has a very strong effect on the corrosion potential of zinc. Zinc alloys with up to 30 weight percent cobalt will cathodically protect steel.

From the results of Co and some other metal additions to zinc it is apparent that noble alloy additions cause the potential of zinc to change to more noble values.

Figure 8:
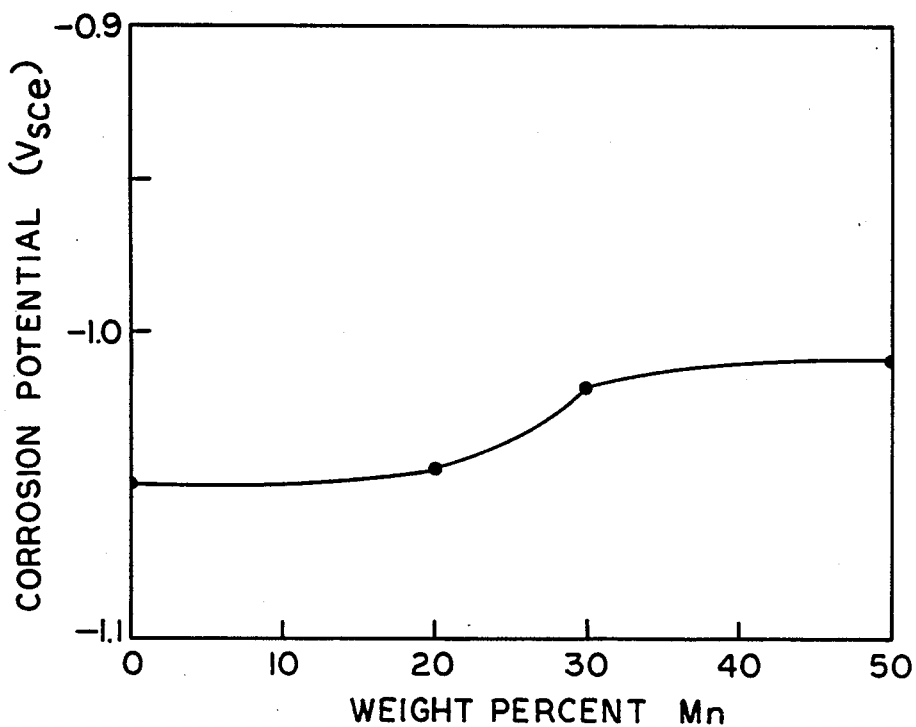
FIG. 8 presents a data plot of solution potential of zinc-manganese alloys as a function of manganese content in air saturated 3.5% sodium chloride solution at 25 C, FIGS. 9A and 9B provide plots of open circuit potential for DQSK steel and Zn-15 Co, coupled potential for Zn-15Co/steel galvanic couple and galvanic corrosion current respectively as a function of time in aerated 3.5% NaCl solution at 25 C.

Data for zinc-manganese alloys was determined, as provided in FIG. 8. Manganese has a solution potential of $-1.2$ Vsce in air-saturated salt water solutions. This potential is electronegative to zinc's potential of $-1.05$ Vsce. The addition of manganese to zinc causes zinc's corrosion potential to change to more electropositive values. It appears that when manganese is added to zinc there is a reversal of manganese's electrochemical properties. It acts as a noble metal alloy addition.

ZERO RESISTANCE AMMETER (ZRA) DETERMINATIONS

ZRA data gives a more complete picture of the degree of galvanic corrosion. The galvanic series (i.e. solution potentials) only indicate which alloy compositions are cathodic to steel.

Figure 9A:
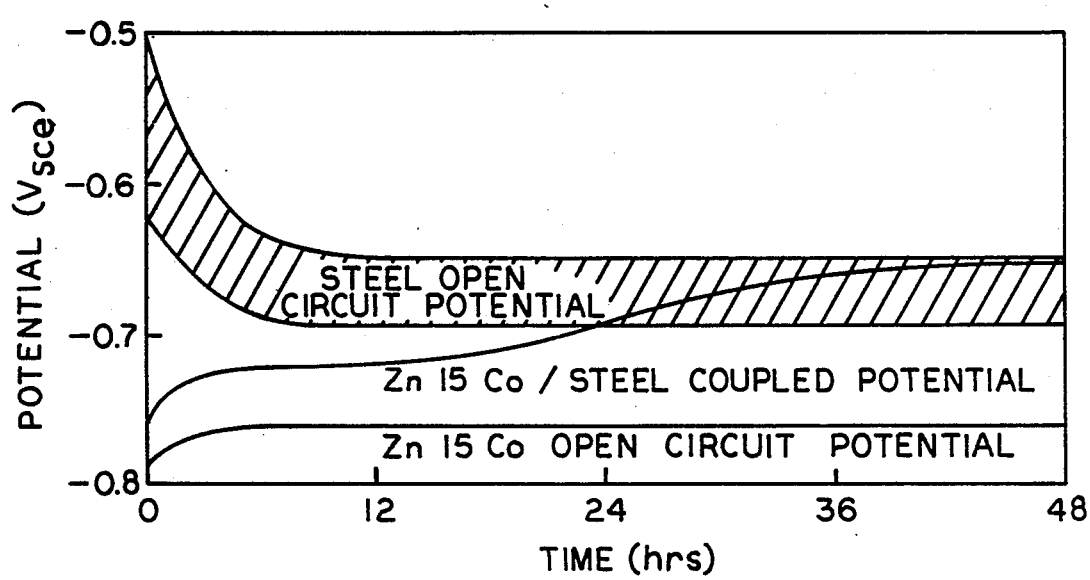
Figure 9B:
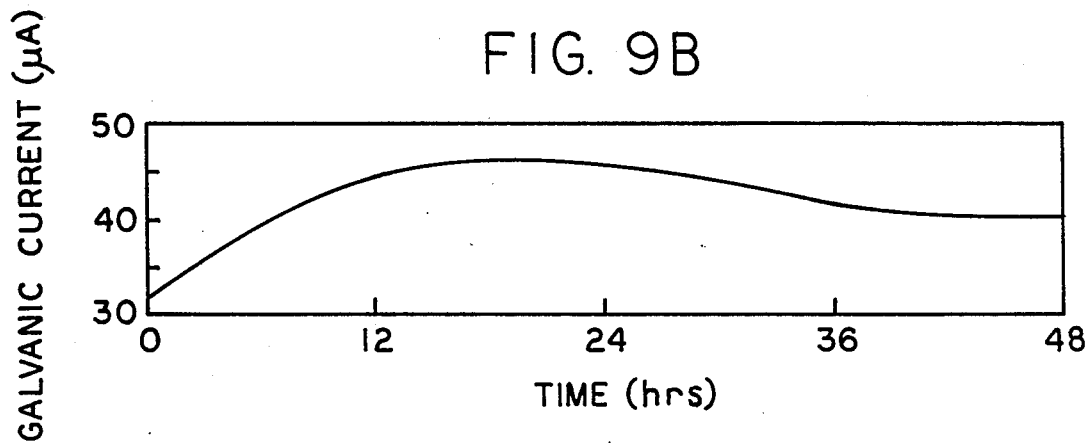
Figure 10:
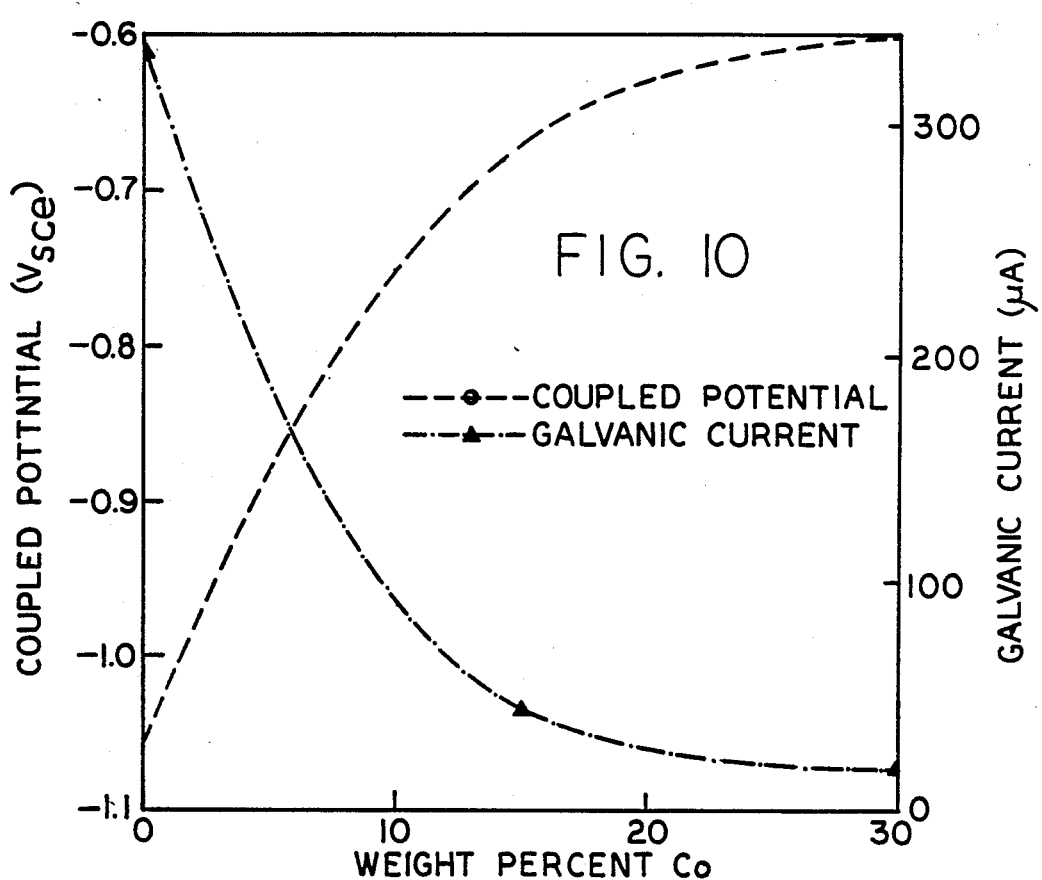
FIG. 10 presents a data plot of galvanic current and coupled potential for Zn/Co alloys coupled to steel in aerated 3.5% NaCl solution.
Figure 11:
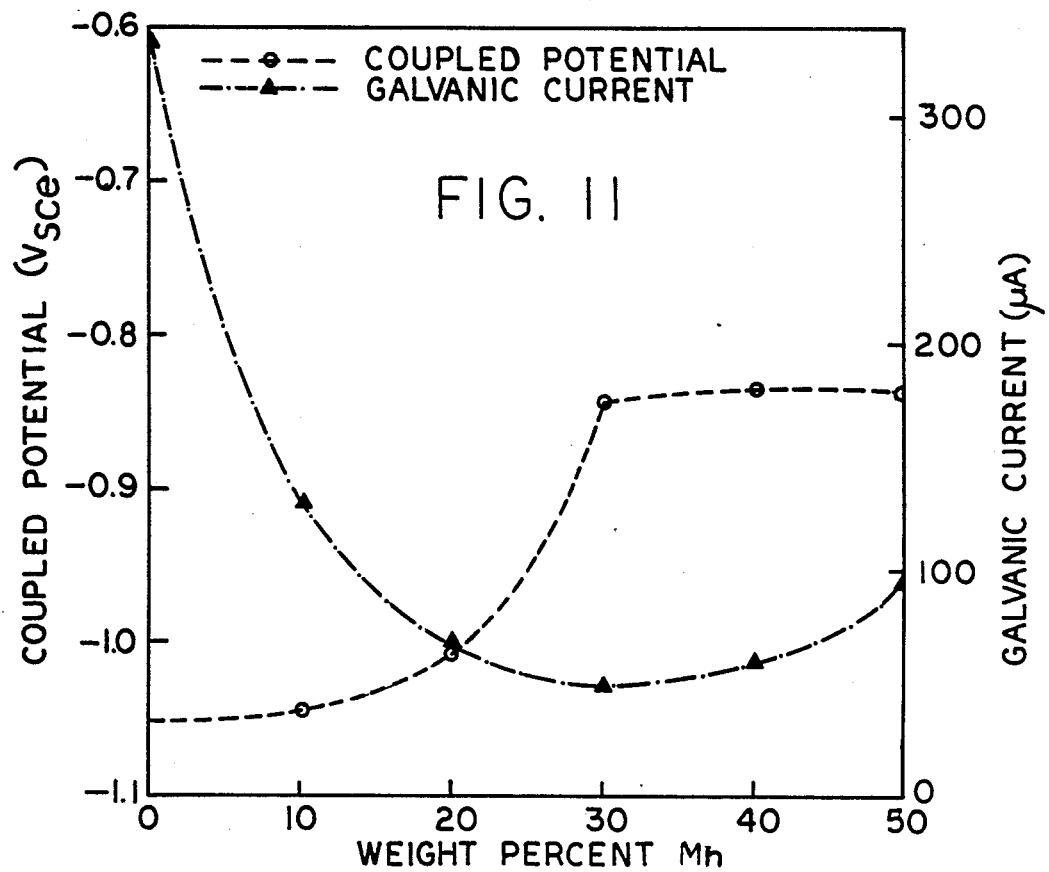
FIG. 11 presents a data plot of galvanic current and couple potential for Zn/Mn alloys coupled to steel in aerated 3.5% NaCl solution.

FIGS. 9 through 11 show the galvanic corrosion current and coupled potential for Zn/Co and Zn/Mn binary alloys, as a function of alloy composition. An initial observation indicates that pure zinc has a rather high galvanic current (about 320 microamps). In general, it may be observed that the addition of either Co or Mn as an alloying element reduced the galvanic corrosion current. It appears that the reduction of the galvanic current with alloying is independent of whether the alloying element is more active or noble than zinc.

Zn-15 Co alloys experience a drop in coupled potential as a function of time as seen in FIG. 9. The change in coupled potential for the Zn-15 Co alloy is not as rapid as observed with some other binary zinc alloys. It is contemplated that this may provide longer lives for Zn-15 Co alloys. The galvanic currents also appear to be smaller for the Zn-15 Co alloy. This may translate to a longer coating life. From FIG. 10, it may be seen that the optimal zinc-cobalt alloy composition lies in the range of 10 to 15 weight percent cobalt.

FIG. 11 displays the galvanic current and coupled potential for Zn/Mn alloys as a function of Mn content. Manganese has a great effect on the galvanic current of zinc. The zinc $-30$ weight percent manganese composition appears to be an optimal for use as a galvanic coating alloy. It has a low galvanic current of 50 microamps and a coupled potential of $-0.850$ Vsce.

POLARIZATION DETERMINATIONS

Figure 12:
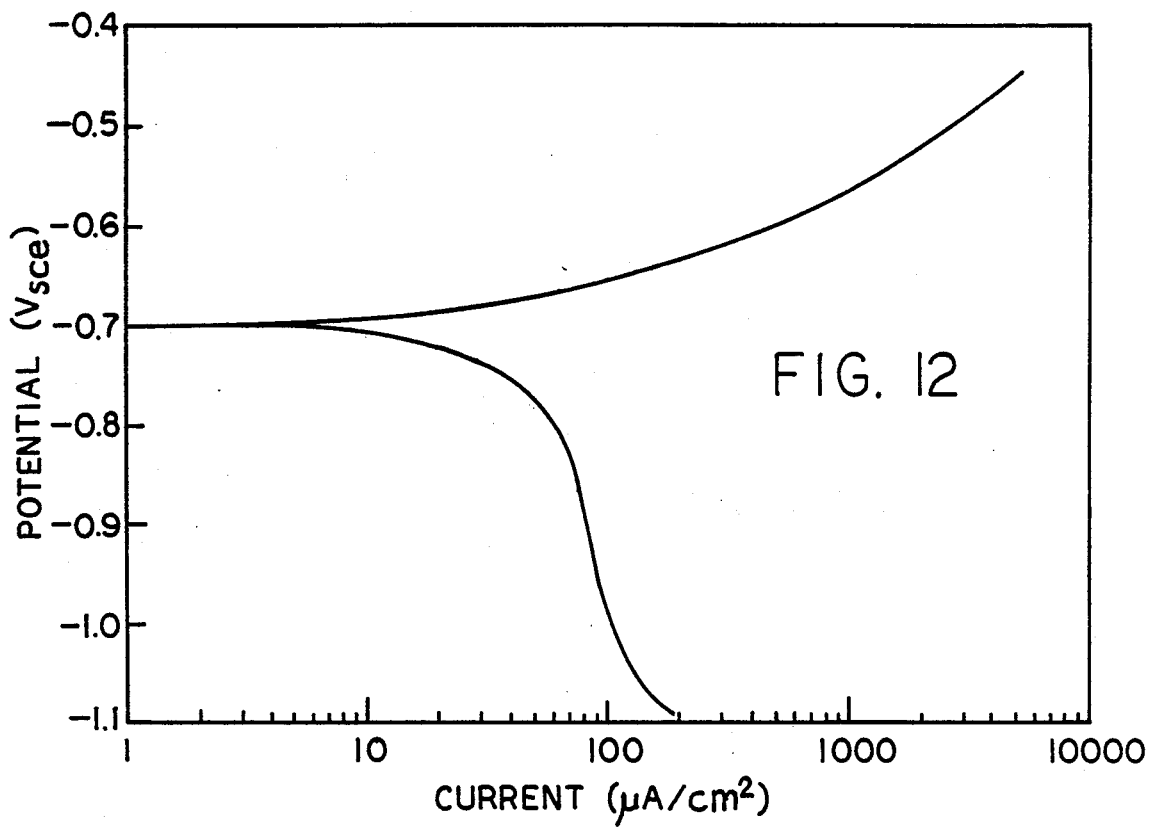
FIG. 12 provides anodic and cathodic polarization curves for DQSK steel in air saturated 3.5% NaCl solution at 25 C, FIG. 13 provides anodic and cathodic polarization curves for pure zinc in air saturated 3.5% solution at 25 C, FIG. 14 provides the anodic polarization curve for Zn-15 Co in air saturated 3.5% NaCl solution at 25 C, and FIG. 15 provides the anodic polarization curve for Zn-30 Mn in air saturated 3.5% NaCl solution at 25 C.

Polarization data for Zn and the alloys of concern were determined to give insight on how polarization affects galvanic coupling. FIG. 12 shows cathodic and anodic polarization curves for DQSK steel. Through Tafel slope extrapolation, the estimated corrosion current for DQSK steel in aerated salt water is on the order of 100 microamps/sq cm. The shape of the cathodic curve is of particular interest as it shows a limiting current density due to the diffusion controlled oxygen reduction reaction. This limiting current density plays a vital role in the magnitude of the galvanic current.

Large current densities associated with the anodic polarization of zinc and the zinc alloys resulted in the early termination of anodic polarization curves. As can be noted from FIGS. 13 through 15, the Tafel portion of the anodic polarization curves continue for about 1 decade. To properly assess Tafel slopes and corrosion currents, the Tafel portion of the anodic curve should continue for at least two decades. Tafel slope extrapolation of the cathodic curves are not possible due to the limiting current density. From the data obtained here we can only quantify the order of magnitude of the corrosion current density.

Corrosion current densities were calculated through linear polarization (M. Stern, A. L. Geary, J. Electrochem. Soc., Vol. 105, p. 638, 1958) using the following equation:

$$\frac{\Delta E}{\Delta I_{appl}} = \frac{B_a B_c}{2.3 I_{corr}(B_a + B_c)}$$

where $\Delta E/\Delta I_{appl}$ is the slope of the polarization curve for the first 10 mV. Both the anodic Tafel slope, $B_a$, and the cathodic Tafel slope, $B_c$, were assumed to be equal to 0.12 V/decade. Stern and Weisert (Proc. ASTM, Vol. 59, p. 1280, 1959) have shown that this assumption results in a corrosion rate that differs from the actual corrosion rate by no more than a factor of three, Icorr is equal to the corrosion rate.

Figure 13:
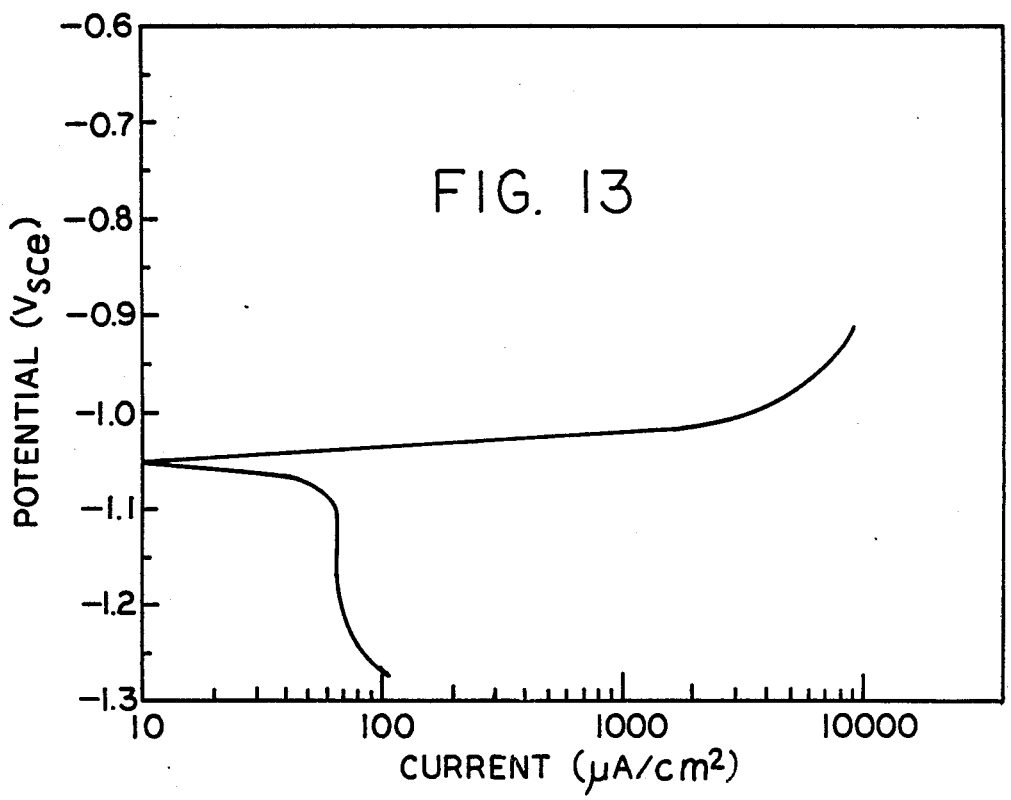

The cathodic and anodic polarization curves for zinc are shown in FIG. 13. Through linear polarization, the estimated corrosion current density is on the order of 150 microamps/sq cm. The shape of the anodic curve indicates that zinc does not polarize easily. This means that steel, in galvanic coupling situations, will cathodically polarize to an active potential close to that of zinc's open circuit potential. By looking at the polarization curves for zinc and steel, it may be visualized that the anodic curve for zinc will intersect the cathodic curve for steel at relatively high currents. This explains the high galvanic current produced in a galvanic couple between zinc and steel.

Based on galvanic coupling experiments: (Zn/ (10 to 15) Co and Zn/ (30 to 40) Mn are considered to be useful galvanic coating alloys. Anodic polarization curves for alloys in these composition ranges are provided in FIGS. 14 and 15. For comparative purposes, the corrosion current densities for each of these alloys is listed in Table II below.

TABLE II

CORROSION CURRENT DENSITY OF DQSK STEEL, ZINC AND SEVERAL ZINC ALLOYS

| MATERIAL | E (mVsce) | Iappl (mA/SQ CM) | Icorr (uA/sq cm) |
|---|---|---|---|
| DQSK steel | 10 | 0.007 | 90 |
| zinc | 7 | 0.040 | 150 |

TABLE II-continued

CORROSION CURRENT DENSITY OF DQSK STEEL, ZINC AND SEVERAL ZINC ALLOYS

Figure 14:
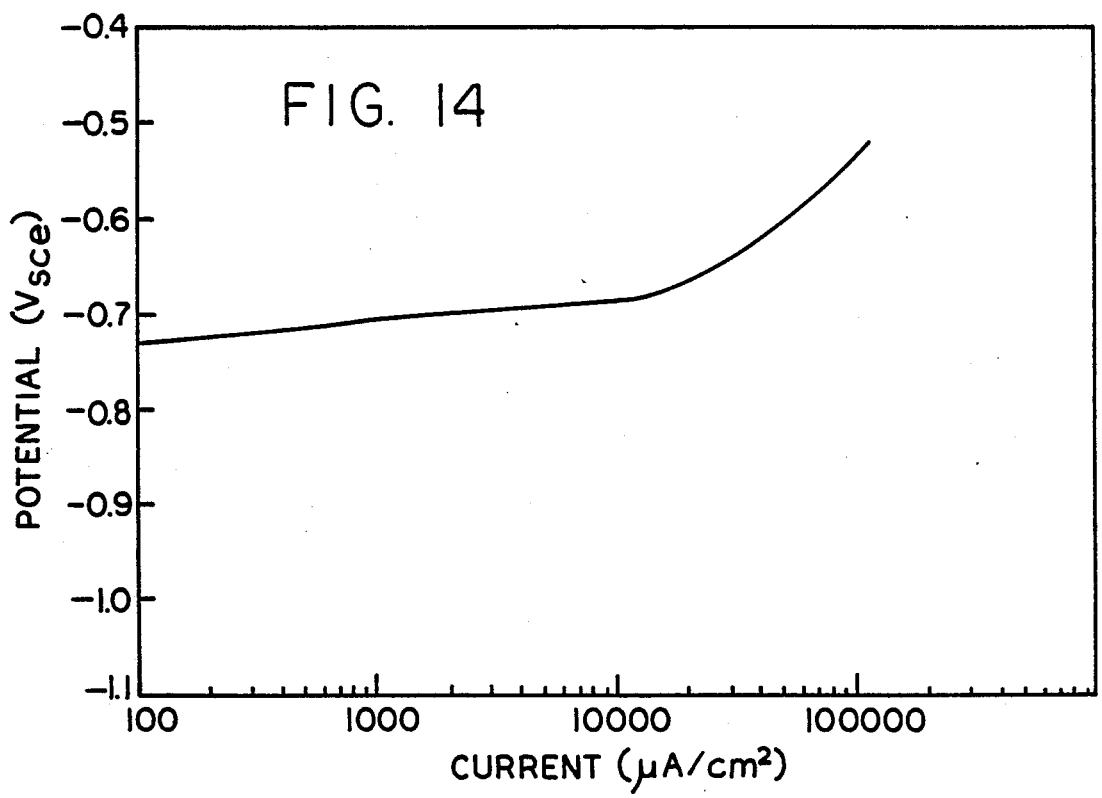

The polarization curve for Zn-15 in FIG. 14 is similar to that noted in another binary zinc alloy. Corrosion current density of about 370 microamps/sq cm appears to be relatively larger than that of the other binary zinc alloy. The polarizability appears to have increased slightly compared to zinc. Lower galvanic current densities associated with this alloy may be attributed to the increased polarizability and the shift in the open circuit anode potential to a more noble value.

Figure 15:
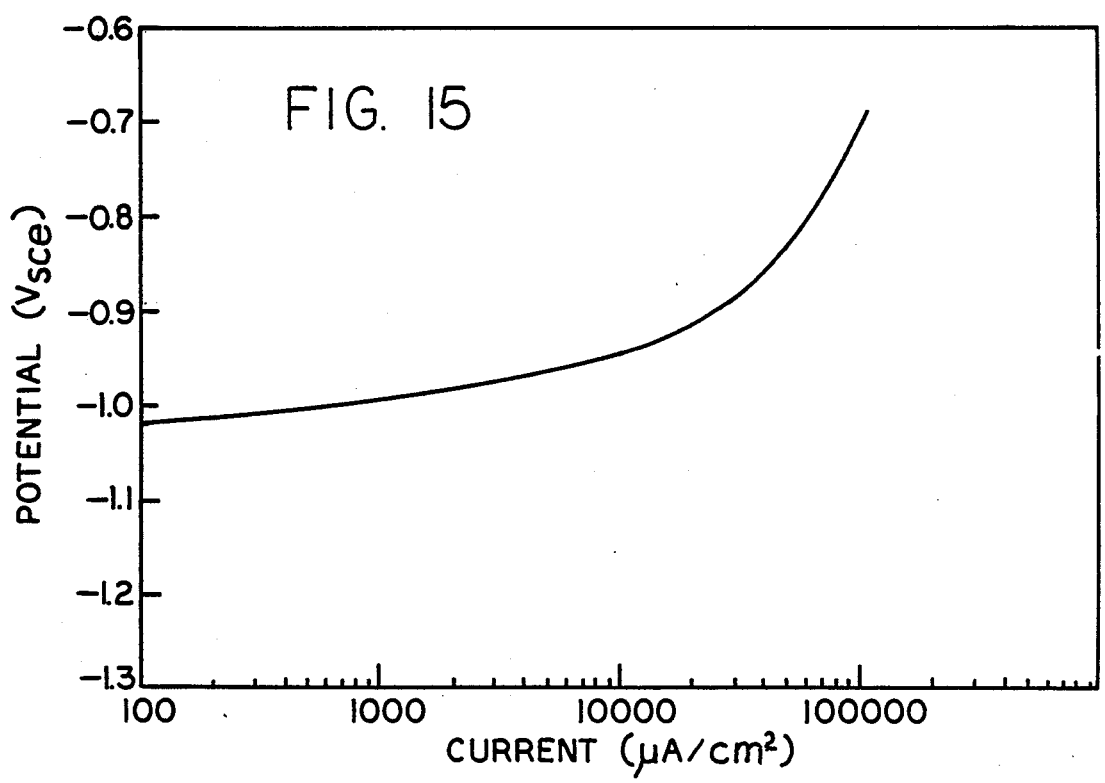

The effect manganese on the polarization of zinc is shown in FIG. 15. The anodic curve shows a great increase in the polarizability. This explains why the n/Mn coupled potentials are much more noble than the open circuit anode potentials. A result of the high degree of polarizability of n/Mn alloys is that the galvanic corrosion rate is reduced greatly compared to pure zinc. The corrosion current density of about 430 microamps/sq cm appears slightly larger than that of Zn or Zn/Co.

It will be apparent to those skilled in the art from the foregoing that numerous improvements and changes can be made in the embodiments described of the invention without departing from the true scope of the invention. Accordingly, the foregoing disclosure is to be construed as illustrative and not in a limiting sense with the scope of the invention being defined solely by the appended claims.

We claim:

1. A method of protecting steel, other than stainless steel from corrosion, which method comprises:
   (a) coating the steel directly on with an alloy selected from the group of alloys which consist essentially of 8–18 %/wt of cobalt and a balance of zinc, and 20–50 %/wt of manganese and a balance of zinc.

2. The method of claim 1 which for said coating employs an alloy consisting essentially of about 11–16 %/wt of cobalt and a balance of zinc.

3. The method of claim 1 which for said coating employs the alloy consisting essentially of about 25–40 %/wt of manganese and a balance of zinc.

4. Steel, other than stainless steel, having adhered directly on a coating of a protective alloy selected from the group of alloys consisting essentially of 8–18 %/wt of cobalt and a balance of zinc, and 20–50 %/wt of manganese and a balance of zinc.

5. The steel of claim 4 in which the adhered directly on coating of the alloy consists essentially of about 11–16 %/wt of cobalt and a balance of zinc.

6. The steel of claim 4 in which the adhered directly on coating of the alloy consists essentially of about 25–40 %/wt of manganese and a balance of zinc.

7. A galvanic coating alloy selected from the group of alloys, which consists essentially of
   (a) 11–16 %/wt of cobalt and a remainder of zinc, and
   (b) 25–50 %/wt of manganese and a remainder of zinc.

* * * * *